United States Patent [19]

Zenz

[11] Patent Number: 4,834,722
[45] Date of Patent: May 30, 1989

[54] INJECTION ASSEMBLY FOR BLOCKING PERIPHERAL NERVES, FOR INSTANCE FOR PLEXUS ANAESTHESIA

[76] Inventor: Michael Zenz, Am Meersmannufer 28, D-3000 Hannover 58, Fed. Rep. of Germany

[21] Appl. No.: 142,311

[22] Filed: Dec. 28, 1987

Related U.S. Application Data

[63] Continuation-in-part of Ser. No. 355,254, Mar. 5, 1982, abandoned.

[30] Foreign Application Priority Data

Mar. 7, 1981 [DE] Fed. Rep. of Germany ... 8106577[U]

[51] Int. Cl.⁴ ............................................. A01M 5/00
[52] U.S. Cl. .................................. 604/272; 604/239; 604/283
[58] Field of Search ............... 604/239, 240, 241, 272, 604/273, 274, 904, 280, 283; 128/339

[56] References Cited

U.S. PATENT DOCUMENTS

| | | | |
|---|---|---|---|
| 2,711,733 | 6/1955 | Jacoby Jr. | 604/274 |
| 3,186,408 | 6/1965 | Jacob | 604/240 |
| 3,638,650 | 2/1972 | Burke et al. | 604/240 |
| 4,296,949 | 10/1981 | Muerterties et al. | 604/905 |

FOREIGN PATENT DOCUMENTS 2067542 8/1971 France .

OTHER PUBLICATIONS

M. J. Cousins and P. O. Bridenbaugh, "Neural Blockade", 1980, pp. 296-310.

Primary Examiner—Stephen C. Pellegrino

[57] ABSTRACT

An injection device is described for the blocking of peripheral nerves, e.g., for plexus anaesthesia. This injection device has an injection needle of metal which is provided at one end with a needle tip and at the opposite end with a base part for the connection of a syringe. In order in this injection device to largely eliminate the danger of damage to nerve fibers or injury to blood vessels by the injection needle and to permit an additional aid by the positive location of the plexus, the needle tip is formed by a ground surface inclined at an angle of 40° to 60°, preferably of 45° to 50°, to the cannula axis.

13 Claims, 1 Drawing Sheet

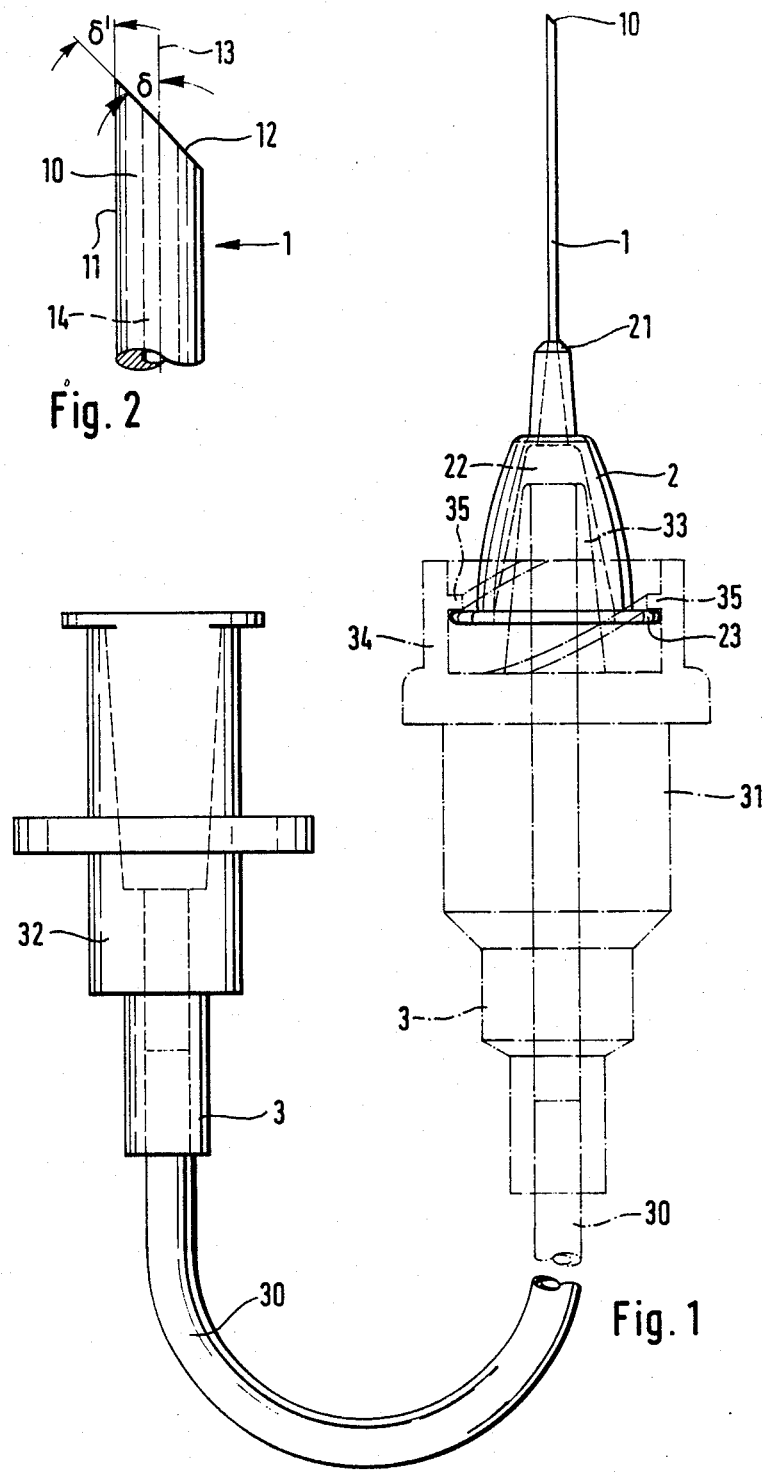

INJECTION ASSEMBLY FOR BLOCKING PERIPHERAL NERVES, FOR INSTANCE FOR PLEXUS ANAESTHESIA

This application is a continuation-in-part of application Ser. No. 355,254, filed Mar. 5, 1982, now abandoned.

BACKGROUND OF THE INVENTION

1. Field of the Invention

The invention relates to the field of the blocking of peripheral nerves, for example the field of plexus anaesthesia, and especially to an injection device having an injection needle of metal which has at one end a base for the attachment of a syringe, and at the opposite end an especially shaped needle tip.

2. State of the Art

Plexus blocks are used in anaesthesia in operations on the arm and hand, for example, especially when urgent operations must be performed on patients who are not fasting. In spite of undisputed advantages, plexus blocks with so-called immobile needles have been successfully practiced only in exceptional cases and by very experienced anaesthetists, since the tip of the injection needle or cannula has, under certain circumstances, caused severe injuries to the nerve fibers and blood vessels as well as degenerative changes in and discontinuities of the fibers.

Conventional injection needles usually have a tip which is defined by a cylindrical circumferential surface and a surface made by grinding at an angle of less than 20° to the cannula axis. The inventor has found through tests that the main reason for lesions to nerve fibers and blood vessels in plexus anaesthesia using the known injection needles is that the needles have very sharp tips. Such sharp needle tips "skewer" even thin nerve fibers and blood vessels instead of turning them aside.

SUMMARY OF THE INVENTION

It is an object of the invention to create an improved injection device for the blocking of peripheral nerves.

It is another object of the invention to construct the needle tip such that the danger of nerve lesion is reduced or even largely eliminated, and an additional aid is created by the positive location of the plexus.

An additional object of the invention consists in providing the injection cannula with a short and flexible prolongation through a LuerLok coupling, so that the cannula can be held in position unaffected by the palpation.

An injection device is offered for the blocking of peripheral nerves, e.g., for plexus anaesthesia. This injection device has a needle of metal which is provided at one end with a sharp tip and at the opposite end with a base for the attachment of a syringe. The needle tip is defined by an approximately cylindrical circumferential surface and a surface made by grinding which is inclined at a relatively blunt angle of approximately 40° to 60° degrees from the needle or cannula axis. The relatively blunt bevel on the needle tip offers a greater resistance to the piercing of the skin than conventional needles. A nerve will roll aside from the approaching injection needle and its beveled tip, so that the needle tip moves past the nerves without damaging or injuring them. Another important advantage of the relatively blunt bevel of the tip of the needle is that the vasculonervous sheath that must be pierced by the needle in a plexus block can be pierced only with a perceptible resistance. When the vasculonervous sheath is penetrated, this resistance produces a perceptible "pop" which is a reliable indication that the cannula tip has penetrated into the nerve sheath and has reached the site intended for the injection.

For the prevention of damage to the nerves or vessels, all that is necessary is that the bevel at the outermost end of the needle tip be made at a relatively blunt angle to the needle axis or adjacent circumferential surface of the needle. The rest of the bevel, however, could be made at a lower or sharper angle. Making the entire bevel surface at a blunt angle increases the resistance produced in the piercing of the vasculonervous sheath and thus improves the reliability of the identification of the plexus that is to be blocked.

For the use of the injection needle of the invention as an "immobile needle", a flexible plastic tube approximately 25 to 35 cm long is connected by means of a Luer-Lok fitting to the base part of the injection needle in a leak-proof manner. At the opposite end of the tube, the injection syringe is also fastened by a Luer-Lok fitting. The flexible extension makes it possible for the injection needle to be held in position unaffected by the palpation.

By means of the invention, therefore, the possibilities for the use of immobile needles are substantially expanded and the plexus block is simplified to such an extent that it can be performed even by less experienced physicians without dangerous side effects for the patients.

These and other objects and advantages of the invention will become more apparent if they are considered in conjunction with the following detailed description of the preferred embodiment of the invention.

BRIEF DESCRIPTION OF THE DRAWING

FIG. 1 is a diagrammatic representation of an embodiment of the injection device of the invention, without an injection syringe, and FIG. 2 is a greatly enlarged view of the portion of the injection needle forming the tip, as seen in the plane of the ground bevel.

DETAILED DESCRIPTION OF THE INVENTION

An embodiment of the injection device of the invention is shown diagrammatically in FIG. 1. It has a needle 1 of metal, referred to hereinafter as the "cannula", which is provided at one end with a base part 2 of plastic. The base 2 can be cemented, for example, to the metal cannula. An injection syringe, not represented in the drawing, can be connected to the base 2 either directly by a Luer-Lok fitting or through an extension designated generally by the reference number 3.

The cannula 1 has on its free end a relatively short needle tip 10 defined by a circumferential surface 11 and a ground bevel 12 intersecting the latter (FIG. 2). The intersection between the bevel surface 12 and the circumferential surface 11 of the cannula 1 can be slightly rounded or dulled at the outermost end in order further to reduce the danger of producing nerve lesions by the use of the injection device. The bevel 12 is at a relatively blunt angle $\delta$ to the cannula axis 13, so that the apex angle $\delta' = \delta$ is relatively blunt. In the case of an embodiment that has proven practical, $\delta$ is approximately 45°; the angle $\delta$ should preferably range from about 40° to about 60°. The size of the cannula 1 that has been tested in practice is 25×0.55 mm, 24 gauge, so that at a bevel angle δ=δ'=45° a bevel 12 is formed which covers 0.55 mm of the length of the cannula. Also 26 gauge has been shown to be useful, or 25 gauge. Further experiments have shown that the maximum outer cannula diameter e should be about 0.55 mm, and the length of the cannula should be in the range of from 25 to 50 mm. The preferred needle length is 35 mm. This is in contrast to epidural needles which have a size from 16 to 19 gauge.

The relatively blunt bevel angle δ, which is more than twice as great as the angle of the bevels of conventional injection needles (δ<20°), is important chiefly at the outermost end of the needle tip 10, i.e., in the left half, as seen in FIG. 2, of the needle between the circumferential surface 11 and the cannula axis 13. The remainder of the bevel 12, however, could be at a lower or more acute angle. The relatively steep slope of the entire bevel 12 with respect to the cannula axis 13 as represented in FIG. 2 is preferred, however, since this increases the resistance encountered upon piercing through the vasculonervous sheath and thus improves the reliability of the location of the plexus that is to be blocked.

The base part 2 is cemented to the end of the cannula opposite the tip 10, at the point marked 21. The cannula bore 14 (FIG. 2) terminates in a tapered socket 22 in the base part 2. The tapered socket 22 terminates in a mounting flange 23 which, in a Luer-Lok fitting, participates in the positive attachment either of the injection syringe or of the flexible extension tube 3.

By means of the flexible tube connection 3 represented in FIG. 1, the cannula 1 can be used as an immobile needle and thus is especially suitable for the blocking of peripheral nerves.

The extension 3 consists of a flexible plastic tube 30 of a length of about 20 to 35 cm, whose ends are attached to complementary fittings 31 and 32 of a Luer-Lok coupling. The fitting 31 is coupled to the base part 2 by fitting a tubular tapered chuck 33 into the tapered socket 22, thereby producing a leak-proof junction between the parts. The axial thrust required for the purpose is produced by a screw cap 34 which is part of the fitting 31 and whose helical internal thread 35 engages the flange 23 of the needle base 2.

The fitting 32 on the opposite end of the tube 30 is of a configuration similar to that of the base 2 of the cannula, so that the chuck of the injection syringe can be coupled to the fitting 32 the same as it can to the base part 2. When the injection needle 1 is joined by the extension 3 to an injection syringe not shown in the drawing, the needle can be held still in its proper place during palpation and is not directly affected by the movements of the syringe. It is important for the length of the tube 30 with the fittings 31 and 32 to be just sufficient—namely not longer than 35 cm—such that it does not interfere with the use of the injection device, but on the other hand the position of the cannula 1 will not be disturbed by unavoidable movements of the syringe.

In the foregoing description the invention has been explained in conjunction with an especially preferred embodiment. It is to be noted, however, that the special details set forth are only for purposes of illustration and the invention can be embodied in other ways without departing from the idea of the invention and from the scope of the appended claims.

I claim:

1. A plexus anaesthesia needle for the injection of a local anaesthetic for blocking peripheral nerves, said needle consisting of metal and having a first end with means for connection of a syringe and a free second end with a needle tip, a continuous passage extending along an axis from the first end to the needle tip, the length of said needle between said first end and said needle tip being approximately 25 to 50 mm; said needle being of a size gauge 24 to 26 and having an outer diameter of approximately 0.55 mm; said needle tip being formed by a circumferential surface of said needle substantially coaxial with said axis and a ground surface inclined at an angle to said axis;
   wherein the improvement comprises: the angle of inclination of said ground surface to said axis ranging from 40° to 60° such that, at least in the area of the outermost end of the needle tip, a nerve will tend to roll away from the inclined ground surface as the needle tip approaches, and the needle tip is moved past the nerve without nerve lesions.

2. A plexus anaesthesia needle according to claim 1, in which said angle of inclination ranges between 45° and 50°.

3. A plexus anaesthesia needle according to claim 1, in which the outermost end of the needle tip is slightly rounded or dulled.

4. The combination of:
   (a) a plexus anaesthesia needle for the injection of a local anaesthetic for blocking peripheral nerves, comprising: a substantially cylindrical injection needle of metal having a first end on which a needle tip is formed, a second end on which a connection portion is formed, and a needle bore extending longitudinally approximately concentrically through said needle substantially to both needle ends, the length of said needle between said needle ends being approximately between 25 and 50 mm; said needle being of a size gauge 24 to 26 and having an outer diameter of approximately 0.55 mm; said needle tip being defined by a circumferential surface of said needle substantially concentric with a longitudinal axis of the needle bore and a ground surface inclined at an angle to said axis;
   (b) a connection component of plastic for receiving the local anaesthetic and for introduction of the anaesthetic into the needle bore, said connection component being glued or cemented to the second end of the injection needle and having a central tapered socket which communicates with the bore and flares funnel-wise toward the receiving side; and
   (c) a prolongation structure for connecting a syringe containing the local anaesthetic to said connection component, the prolongation structure containing an elongated, flexible conduit in the form of a flexible plastic tube to whose one end first coupling means are disposed for releasable coupling with said connection component and on whose other end second coupling means are disposed for releasable connection of a syringe, said flexible plastic tube helping to hold the injection needle immobile upon a movement of the second coupling means;
   wherein the improvement comprises: the angle of inclination of the ground surface to the needle axis ranging between 40° to 60°, thereby reducing the danger of nerve lesions and facilitating the location of the plexus.

5. The combination according to claim 4, wherein the tapered socket of the connection component is limited outwardly by a fastening flange, the first coupling means having an axially projecting tubular tapered chuck communicating with the flexible tube, said chuck being adapted to be inserted into the tapered socket axially, and a screw cap concentrically surrounding the tubular tapered chuck at a distance therefrom, which is adapted to be screwed onto the fastening flange of the connection component, thereby drawing the tubular tapered chuck into the tapered socket and producing a leak-proof coupling between the chuck and the tapered socket.

6. The combination according to claim 5, wherein said second coupling means of the prolongation structure have a tapered socket limited by a fastening flange, and having the same shape and construction as said connection component and flaring funnel-wise toward the receiving end.

7. The combination according to claim 4, wherein said flexible plastic tube has a length ranging from about 20 to 35 cm.

8. The combination according to claim 4, in which said angle of inclination is 45° to 50°.

9. The combination according to claim 4, in which the outermost end of the needle tip is slightly rounded or dulled.

10. An injection device for the blocking of peripheral nerves, comprising:
(a) a substantially rigid injection needle of metal which has at a distal end a relatively short needle tip and on the opposite end a socket and is provided with an axial bore connecting the two needle ends, the length of said needle between said needle ends being approximately between 25 and 50 mm; said needle being of size gauge 24 to 26 and having an outer diameter of approximately 0.55 mm; said needle tip being defined by a substantially cylindrical circumferential surface concentric with a longitudinal axis of said needle and a ground surface intersecting the circumferential surface at an angle; and
(b) a flexible plastic tube connected in a liquid-tight manner to the connection end of the injection needle and having a length ranging from 20 to 35 cm, to which the end remote from the injection needle is provided with coupling means for the connection of an injection syringe and forms an outwardly leak-proof conduit connection from an injection syringe to the injection needle, means being provided for sealing off the coupling points between the injection needle and the flexible plastic tube as well as at the coupling means of the plastic tube;
wherein the improvement comprises: the angle of inclination of the ground surface to said needle axis ranging from 40° to 60°.

11. An injection device according to claim 10, wherein the length of said needle is 35 mm.

12. An injection device according to claim 10, in which said angle of inclination is 45° to 50°.

13. An injection device according to claim 10, in which the outermost end of the needle tip is slightly rounded or dulled.

* * * * *